United States Patent
Bernhardt

(10) Patent No.: US 10,157,464 B2
(45) Date of Patent: Dec. 18, 2018

(54) DETERMINING A NAVIGATION IMAGE TO BE DISPLAYED

(71) Applicant: Philipp Bernhardt, Forchheim (DE)

(72) Inventor: Philipp Bernhardt, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/418,892

(22) Filed: Jan. 30, 2017

(65) Prior Publication Data
US 2017/0228863 A1 Aug. 10, 2017

(30) Foreign Application Priority Data
Feb. 4, 2016 (DE) .................. 10 2016 201 702

(51) Int. Cl.
*G06T 7/00* (2017.01)
*A61B 6/00* (2006.01)
*G06T 11/00* (2006.01)
*G06T 11/60* (2006.01)

(52) U.S. Cl.
CPC .......... *G06T 7/0016* (2013.01); *A61B 6/5294* (2013.01); *G06T 11/001* (2013.01); *G06T 11/60* (2013.01); *G06T 2207/10116* (2013.01); *G06T 2207/20224* (2013.01); *G06T 2207/30101* (2013.01)

(58) Field of Classification Search
USPC ........................................ 382/128, 130, 132
See application file for complete search history.

(56) References Cited

U.S. PATENT DOCUMENTS 8,036,730 B1 * 10/2011 Damadian ............ A61B 5/0555
324/307
8,175,357 B2 * 5/2012 Ozawa .................. G01N 23/04
378/98.11

(Continued)

FOREIGN PATENT DOCUMENTS

DE 102009037243 A1 2/2011

OTHER PUBLICATIONS

German Office Action for related German Application No. 10 2016 201 702.0 dated Nov. 24, 2016, with English Translation.

*Primary Examiner* — Ishrat I Sherali
(74) *Attorney, Agent, or Firm* — Lempia Summerfield Katz LLC

(57) ABSTRACT

A method is provided for determining a navigation image displaying features of a region of interest of a patient, (e.g., used during a medical intervention). The method includes determining a first subtraction image by recording a first X-ray image with an X-ray device and subtracting a mask image. The method also includes determining a second subtraction image by recording a second X-ray image with the X-ray device and by subtracting the mask image or a further mask image. Additionally, the navigation image is determined by superimposing the first and the second subtraction image. At least one of the subtraction images is preprocessed before the superimposition by transfer from a gray-value space into a color space that is different from a color space of the other subtraction image. The navigation image is determined in color and/or the dynamics of at least one of the subtraction images are compressed.

13 Claims, 3 Drawing Sheets

(56) References Cited

U.S. PATENT DOCUMENTS

| | | | |
|---|---|---|---|
| 8,509,384 B2* | 8/2013 | Spahn | A61B 6/12 378/98.12 |
| 2009/0136102 A1 | 5/2009 | Kimpe et al. | |
| 2011/0038458 A1 | 2/2011 | Spahn | |
| 2016/0078621 A1* | 3/2016 | Nagae | G06T 7/0016 382/130 |
| 2016/0228084 A1* | 8/2016 | Nempont | A61B 6/461 |

* cited by examiner

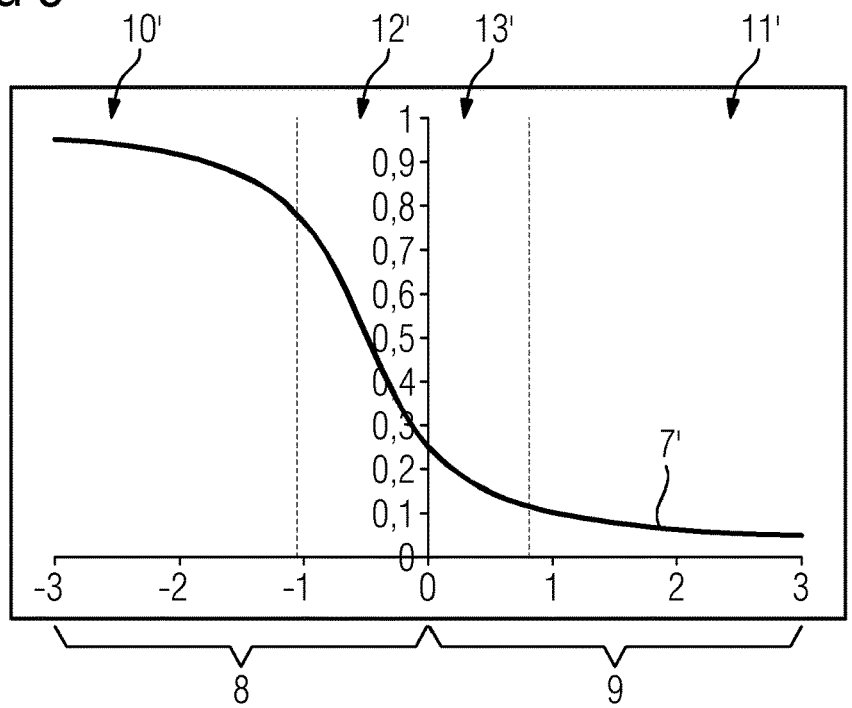
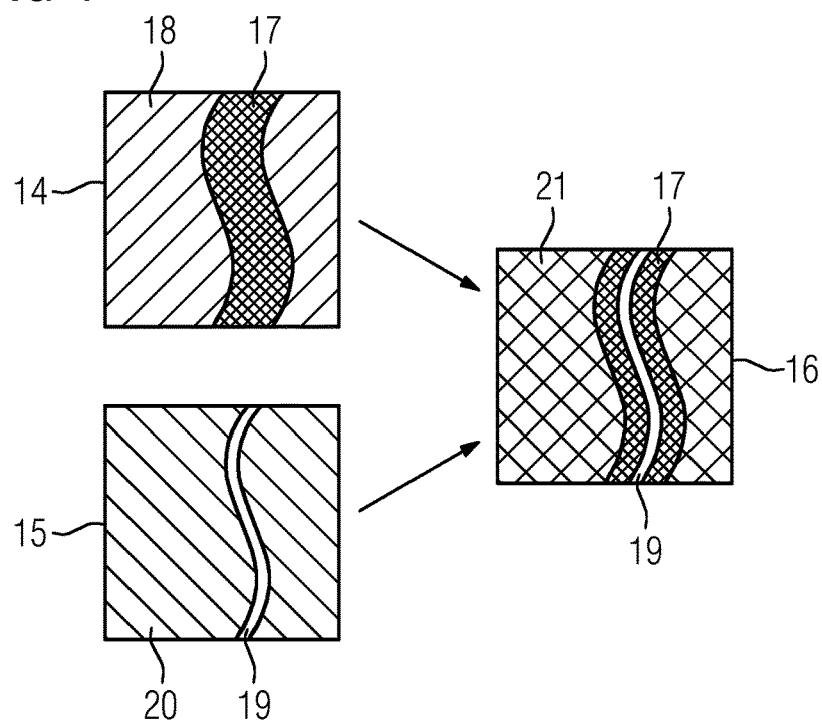

DETERMINING A NAVIGATION IMAGE TO BE DISPLAYED

The application claims the benefit of DE 10 2016 201 702.0, filed Feb. 4, 2016, which is hereby incorporated by reference in its entirety.

TECHNICAL FIELD

The disclosure relates to a method for determining a navigation image displaying features of a region of interest of a patient, (e.g., used during a medical intervention), wherein: a first subtraction image is determined by recording a first X-ray image with an X-ray device and subtracting a mask image; a second subtraction image is determined by recording a second X-ray image with the X-ray device and by subtracting the mask image or a further mask image; and the navigation image is determined by superimposing the first and second subtraction image. The disclosure also relates to an X-ray device, a computer program, and an electronically readable data medium.

BACKGROUND

In medical X-ray-based imaging, subtraction techniques are used in body regions where there is relatively little movement, e.g., in the field of neurology. This means that the X-ray device first records an anatomical mask image. Then, a slight change is made in the body region, (e.g., a medical instrument visible in X-ray images is moved), a therapeutic and/or diagnostic measure is performed or a contrast medium is injected. If the mask image is then removed from X-ray images that have been recorded with the X-ray device, only the change remains visible. This enables fixed, anatomical structures, (e.g., bones), to be eliminated. It is, for example, possible to generate subtraction images that only show the blood vessel system, a medical instrument, and/or an introduced therapeutic agent, for example, a vessel sealing system in the region of interest of the patient.

Interventions in the blood vessel system, (e.g., in the region of a patient's head), require extremely precise positioning of medical instruments. To this end, methods are known for monitoring the positioning of medical instruments in the imaging, for example, by recording fluoroscopy images as X-ray images of an X-ray device. This enables the movement of medical instruments, which are visible in fluoroscopy images recorded with low X-ray doses, to be tracked. In this context, for navigation applications for interventions in the human body, so-called double-subtraction techniques have been suggested to be used to enhance the display in this context. With a double-subtraction technique, (for example, the so-called "roadmap" technique), first a subtraction technique with contrast media is used to generate a first subtraction image solely depicting the patient's blood vessels in the region of interest. Using this image or a further mask image, a second subtraction technique is used in which an X-ray image showing a medical instrument, for example a guide wire, is recorded and a second subtraction image is generated, which may be superimposed on the first subtraction image to visualize the medical instrument in the blood vessel system.

Like subtraction images, X-ray images are gray-value images, and hence they reproduce the brightness of structures on a gray scale. If two subtraction images are superimposed, (for example, by adding up their gray values), items may be erased in the depiction. For example, a medical instrument shown in a second subtraction image may have a similar gray value to that of the background in an inverted first subtraction image showing the blood vessel system of the patient in the region of interest. Hence, in a subtraction image of this kind inverted before the superimposition, the vessels are not black, but white, so that, for example, on the superimposition of a medical instrument located at the edge of the vessel, clear differentiation from the directly adjacent background may not be possible: information is lost.

SUMMARY AND DESCRIPTION

The scope of the present disclosure is defined solely by the appended claims and is not affected to any degree by the statements within this summary. The present embodiments may obviate one or more of the drawbacks or limitations in the related art.

The disclosure is based on the object of providing a possibility for the superimposition of two subtraction images in a double-subtraction technique so that as little information as possible is lost from the subtraction images.

To achieve this object, a method provides that at least one of the subtraction images is preprocessed before the superimposition by transfer from a gray-value space into a color space that is different from a color space of the other subtraction image, wherein the navigation image is determined in color and/or the dynamics of at least one of the subtraction images are compressed.

In this context, at least one of the subtraction images may be transferred to a color space. Therefore, the use of color information utilizes a dimension that is simple to add to the navigation image, namely the color, so that it is not only possible to achieve a clear assignment of features visible in the subtraction images to the respective subtraction image, in addition the possibility of information being erased is virtually excluded. Therefore, the navigation image is not, as is conventionally the case, determined as a gray-value image, but as a color image, for example in the red-green-blue (RGB) color space. Further, it is also possible for a red space, a blue space and a green space to be used to define different color spaces as sub-spaces of the RGB color space, wherein the values of the different colors are to be correspondingly linked with one another. For example, a magenta color space is obtained by combining the colors red and blue, the values of which may be selected as the same in a one-dimensional magenta color space.

In this context, two disjoined color spaces may be used for the two subtraction images, wherein an increase in the distance between the color spaces is accompanied by enhanced visibility of the information shown in the navigation image. Moreover, when disjoined color spaces are used, there is no additive increase in the noise and so the existing signal-to-noise ratios remain unchanged.

While dynamic compression may be used additionally to color coding to enhance the navigation image, it is obviously also conceivable for the probability of features being erased or rendered invisible during the superimposition to be reduced solely using dynamic compression. The result of dynamic compression is that the entire gray-value range available is no longer used for the preprocessed subtraction images, but only a sub-range, which may be understood to be a dynamic result range of the dynamic compression. In this case, the original gray values (or, if color coding has already taken place, the color values) are depicted on new gray values (or color values), to which end, as also for the color coding, it is expediently possible to use a look-up table. In this case, dynamic compression may be based on a compression function, which does not mandatorily have to be a straight line, but may obviously have a shape that is adaptable to highlight certain structures. A particularly steep course of the compression function intensifies structures in the dynamic portion in which it occurs, while a somewhat flatter course of the compression function suppresses structures and describes a type of saturation. The possibilities for using special compression functions are discussed in more detail below.

It is in each case also expedient with dynamic compression, for two disjoined dynamic result ranges to be used for the two subtraction images. In this case, a corresponding suitable selection, which may ultimately obviously also be dependent upon the original dynamics of the respective subtraction images, may enable the probability of features that are no longer visible in the navigation image to be further significantly reduced. In this case, it has been shown that it is also possible to obtain outstandingly legible navigation images by procedures in which only a small dynamic result range is used for one of the subtraction images but a larger dynamic result range is used for the other subtraction image.

In the event of a combination of color coding and dynamic compression, it is also particularly expedient for the dynamic compression of the at least one subtraction image to be used to enhance the legibility of the navigation image produced, as is explained in more detail below.

One particularly advantageous field of application of the method is obtained when the first subtraction image is an image of a blood vessel system of a patient, wherein the first X-ray image is recorded as a filled image with the administration of contrast medium in the blood vessel system and/or the second subtraction image is an image showing least one medical instrument located in the vascular system, wherein second X-ray images may be recorded cyclically. In this case, therefore, the navigation image is used for the navigation and tracking of a medical instrument during a medical intervention on the patient. The second X-ray images may then be recorded as fluoroscopy images, therefore with a low dose, so that although the instrument may be identified, the anatomy is displayed rather faintly. However, the first subtraction image provides a clear depiction of the relevant anatomy thus enabling excellent navigation, e.g., due to the good visibility of features, (e.g., information), from both subtraction images because of the preprocessing during the superimposition.

One advantageous development provides that, when features contained in the second subtraction image are displayed against a dark background of the first subtraction image, a color space extending from black to magenta is used for the second subtraction image or, when features contained in the second subtraction image are displayed against a light background of the first subtraction image, a color space extending from white to red is used for the second subtraction image. Experiments have shown that magenta on a dark background is particularly easy to identify and easy on the eye in the display, so that the use of a color space of this kind may be used in certain examples. Further useful color spaces in this context extend from black to yellow and/or from black to cyan. In the opposite case, it was established that red stands out particularly clearly from white.

In one embodiment, in the case of features depicted using a first dynamic portion on a background using a second dynamic portion of the overall dynamic region, in at least one of the subtraction images on at least one of the at least one subtraction image, dynamic compression is used to suppress the structures in a saturation portion of the first dynamic portion bounding the overall dynamic region and in at least one saturation portion of the first dynamic portion bounding the overall dynamic region and to intensify structures in a boundary region of the first dynamic portion positioned adjacent to the second dynamic portion. This is explained by way of example for a subtraction image in which the relevant information, (e.g., the features), stand out in black against a white background, for example in the case of the recording of a patient's blood vessel system using a contrast medium. In this case, therefore, the first dynamic portion is the dark portion, for example the dark half of the overall dynamic region (overall dynamics), while the second dynamic portion is the "light" half of the overall dynamics, e.g., the half tending toward white. If a compression function is used, which in the region of very dark to black structures only has a very small gradient when displayed on new dynamic values of the dynamic result range, structures, (e.g., edges), in this saturation portion of the first dynamic portion are attenuated so that a type of saturation occurs for structures displayed as particularly dark. However, a corresponding saturation or suppression of edges/structures may also take place in the second dynamic portion overall, or at least in a suppression portion of the second dynamic portion, because no relevant structures are expected here in any case. However, it may also be interesting to consider at least an edge portion of the first dynamic region separately, which therefore contain noise and weak structures/features in the dark half of the overall dynamic region. For dark noise and faint structures of this kind in the dark region, it has been found to be particularly advantageous for the compression function to have a steep gradient and therefore structures/edges tend to be intensified. Because the noise overall tends to be homogeneous, coherent, up to now only weakly visualized structures, are in this way highlighted and accentuated. Therefore, white structures and structures in the outermost dark region, (e.g., inside blood vessels), are suppressed and do not interfere with the overall perception of the navigation image produced later. In this case, reference is made once again to the fact it is also possible to provide a steeper gradient, which ultimately results in neither suppression nor intensification, for an edge portion of the second dynamic portion, in which the lighter noise ultimately occurs. Therefore, overall, the dynamic compression is used to enhance the image information further, e.g., to highlight relevant structures more clearly and to suppress less relevant structures. Reference is also made to the fact that the use of a compression function of this kind or a look-up table resulting therefrom is expedient not only for the subtraction image showing the anatomical features, (e.g., the blood vessel system), but may also result in a clear enhancement in the case of subtraction images showing medical instruments as features. Reference is also made to the fact that, when the dynamic portions are selected with the same size, with the embodiment described, the compression function is asymmetric based on the overall dynamic region.

In this context, one expedient development may provide that, in the case of features contained in both subtraction images in the same dynamic portion, at least one subtraction image is inverted before the superimposition within the context of the dynamic compression. Therefore, in this way the possibility is prevented, even in the case of different color coding, of the features remaining in the same dynamic portion in both images and this further greatly enhances the visibility and distinctiveness of features.

In addition to the method, the disclosure also relates to an X-ray device including a control device to carry out the method. For example, the X-ray device may be an X-ray device used for medical interventions, e.g., an X-ray device with a C-arm on which an X-ray source and an X-ray detector are arranged opposite to one another. Therefore, X-ray devices may include a control device in which the navigation image is determined not only by simple superimposition of the subtraction images, but a preprocessing unit is provided, which, for example, able to access look-up tables stored within the control device in order to perform color coding and/or dynamic compression. When different color spaces are used for the subtraction images, the generation unit for the navigation image generates the navigation image in the corresponding colors. The control device is also embodied to control other components of the X-ray device for recording X-ray images, which may also be used as mask images. This may take place by a recording unit.

The disclosure also relates to a computer program, which carries out the acts of the method when the computer program is executed on a computing device, e.g., on a control device of the X-ray device. The disclosure also relates to an electronically readable data medium on which a computer program is stored. This means that, when the electronically readable data medium is stored in a corresponding read device of a computing device, the computing device is configured to implement the method by executing the computer program. The electronically readable data medium may be a non-transitory, e.g., permanent, data medium, such as a CD-ROM.

All explanations relating to the method may be transferred analogously to the X-ray device, the computer program, and the data medium.

BRIEF DESCRIPTION OF THE DRAWINGS

Further advantages and details of the present disclosure may be derived from the exemplary embodiments described below and with reference to the drawing, which shows:

FIG. 3 depicts an example of a second compression function based on a look-up table.

FIG. 4 depicts an example of the combination of subtraction images to form a navigation image.

DETAILED DESCRIPTION

Figure 1:
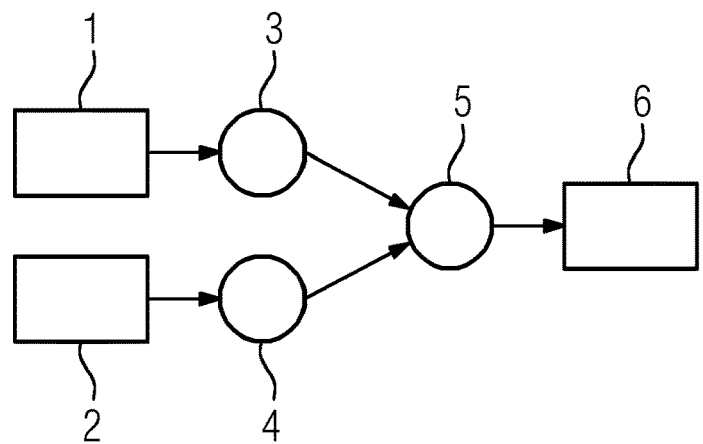
FIG. 1 depicts a diagram explaining the sequence of the method according to an example.

FIG. 1 is a diagram depicting a sequence of a method. In this case, the exemplary embodiments shown here relate to an application in which a navigation image is to be enabled that is as informative and identifiable as possible for monitoring the navigation of a medical instrument in a blood vessel system in a region of interest of a patient. To this end, two subtraction images compiled with an X-ray device are combined, namely a first subtraction image 1 (e.g., a blood-vessel system image) and a second subtraction image 2 (e.g., an instrument image). To determine the subtraction images, X-ray images are recorded in which the desired features, in particular highlighted, may be identified, from which a mask image recorded under the same conditions, without high-lighting or without the medical instrument, which also entails an X-ray image of the region of interest, is subtracted. In the case of the first subtraction image 1, the X-ray image is recorded with contrast-medium-filled vessels of the blood vessel system, so that, following subtraction of the mask image, only the vessels of the blood vessel system are retained as features, e.g., displayed as dark against a white background. The second X-ray image is a cyclically recorded fluoroscopy image, on which the instrument may be identified, from which a fluoroscopy image without an instrument recorded with the same recording parameters is subtracted as a mask image. The result is a display showing the at least one medical instrument, in particular, as dark. Therefore, the subtraction images 1, 2 are initially gray-value images.

The two subtraction images 1, 2 are now first subjected to a preprocessing act 3, 4 in which the gray values of the subtraction images 1, 2 are replaced by new image values by a look-up table. In this context, in the present case, the look-up table used in the preprocessing act 3 only implements a dynamic compression, which will be explained in more detail below, while in the preprocessing act 4, both dynamic compression and the transfer of the grey-value space into a color space, in the example the color space from black to magenta, take place. In addition, the second look-up table inverts the second subtraction image, which means formerly white or light structures are shown as black or dark, while formerly black structures are now shown in light magenta.

It is noted at this point that the look-up table used in preprocessing act 3 may transfer the first subtraction image 1 from the grey-value space into a color space that may be disjoined from the color space into which the second subtraction image 2 is transferred.

In a combination act 5, the preprocessed subtraction images 1, 2 are then combined by superimposition to form one (e.g., colored) navigation image 6 output on a display device and supporting the navigation of a person carrying out the medical intervention. The display device may be a monitor arranged on the X-ray device used.

Figure 2:
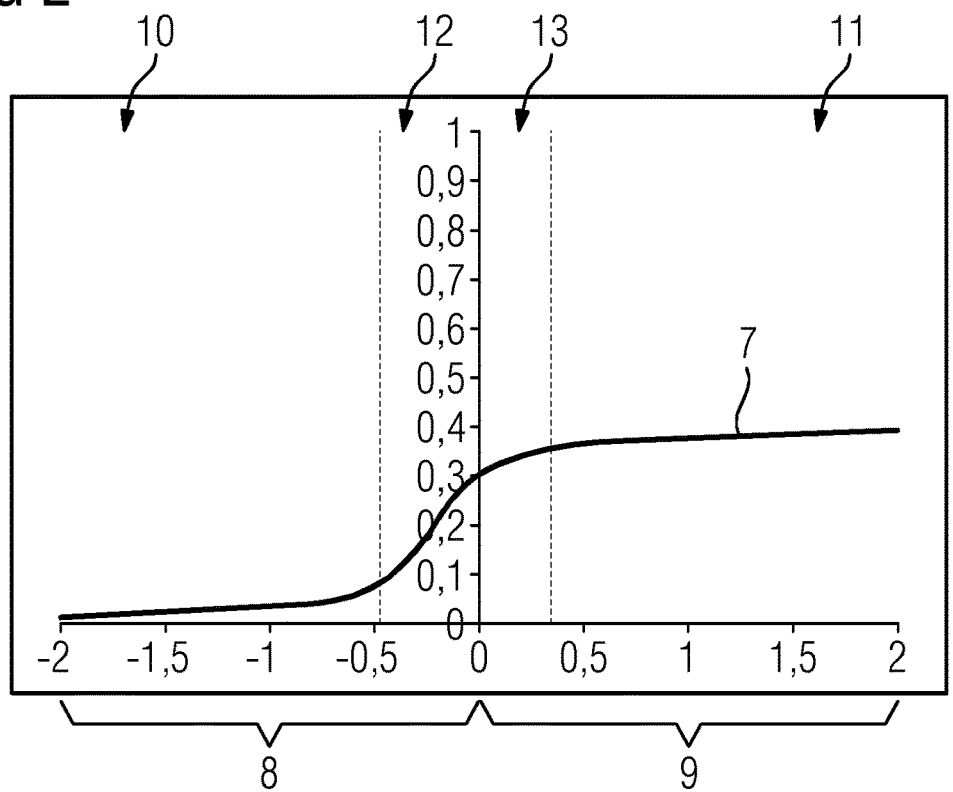
FIG. 2 depicts an example of a first compression function based on a look-up table.

FIG. 2 shows the compression function 7 based on the look-up table used in the preprocessing act 3, which transfers the (e.g., gray value) overall dynamic region used in the first subtraction image 1 in a smaller dynamic result range lying in the region of dark grey tones, which means, that the first subtraction image 1 showing the blood vessel is much darker thus enhancing perceptibility in the navigation image 6. Because the contrast medium results in extreme attenuation of the X-rays, the first subtraction image 1 is characterized by the fact that, as features to be depicted, the vessels of the blood vessel system are depicted as extremely dark—this is in particular the case with expanded vessels, which are ultimately shown as almost black. However, the background is white because all the other structures are subtracted therefrom. However, this means that the overall dynamic region of the still un-preprocessed first subtraction image 1 may be divided into two dynamic portions 8, 9, here a "dark" dynamic portion 8 and a "light" dynamic portion 9. In the present case, the "zero" of the overall dynamic region of the still un-preprocessed first subtraction image 1, which also represents the boundary between the first dynamic portion 8 and the second dynamic portion 9, is selected as the subtraction zero. Here by way of example, a percentage is shown on the horizontal axis, e.g., therefore ultimately a multiplication factor, which is also entered in the look-up table.

It is evident from FIG. 2 that a further subdivision of the dynamic portions 8, 9 takes place in accordance with the course of the compression function 7. For example, both the first dynamic portion 8 and the second dynamic portion 9 have sub-portions directed toward the boundary of the overall dynamic region, here a saturation portion 10 and a suppression portion 11. Both in the saturation portion 10 and in the suppression portion 11, the gradient of the compression function is extremely low, so that structures/edges are suppressed; in particular expanded blood vessels that appear dark in the non-preprocessed first compression image 1 appear more homogeneous, therefore saturated, in the preprocessed first subtraction image 1 following the preprocessing act 3. Structures in the background are suppressed. However, a boundary portion 12 of the first dynamic portion 8 tending toward lighter values is characterized in that here there is a relatively high gradient of the compression curve 7. This boundary portion 12 contains slightly dark structures, e.g., vessels with a small diameter, and "dark" noise. Here the structures are intensified, which means, because the noise may be considered as homogeneous, that small, otherwise more-difficult-to-identify vessels are highlighted in the blood vessel system. On the other hand, a corresponding boundary portion 13 of the second dynamic portion 9 contains "light" noise; here, there is neither intensification nor suppression to any significant degree.

FIG. 3 shows the compression function 7', which was used to determine the look-up table of the preprocessing act 4. In this context, the object here is a color space, which means, the gray values of the still non-preprocessed second subtraction image 2 are transferred by the look-up table to uniformly selected red and blue values in a RGB-color space as a dynamic result range, wherein in the present case at least approximately the entire available magenta dynamics may be used. In other words, the color coding is also depicted by the compression function 7'.

It is also the case with the second subtraction image 2 that the relevant features, here the medical instruments, tend to be depicted dark, while the background appears white. In order to generate a more legible navigation image 6, first reference may be made to the fact that the compression function 7' has an inverse course, which means formerly dark or black structures are depicted in light magenta, while formerly light structures appear in dark magenta tones. In this context, it is also expedient for the available magenta dynamics not to be utilized up to the absolute black tone in order further to support the distinctiveness of structures in the navigation image 6. Because the first and the second subtraction image in which the relevant features are depicted are of the same type, a definition of the first dynamic portion 8 and the second dynamic portion 9 similar to that depicted may be used. Here, the course is selected such that a saturation portion 10', a suppression portion 11', a boundary portion 12' and a further portion 13' are formed so that intensification in the region of slightly dark structures is achieved.

FIG. 4 shows, for purposes of explanation, segments 14, 15 of the preprocessed first subtraction image 1 or second subtraction image 2 and the combination thereof to form a segment 16 of the navigation image 6. The segment 16 contains in an approximately black depiction an expanded vessel 17 against the slightly lighter, but still dark, background 18. In the segment 15, a light magenta instrument 19 is identifiable against a dark magenta background 20. The superimposition of these segments 14, 15 results in a segment 16, in which, on the one hand, the vessel 17 stands out as dark and identifiable from the background 21 (e.g., substantially dark-magenta), while, on the other hand, the instrument 19 that appears in light magenta may be identified in the vessel 17.

Figure 5:
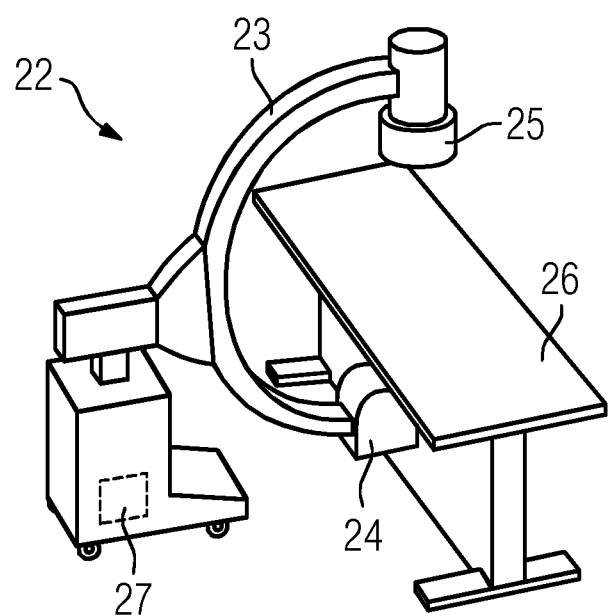
FIG. 5 depicts an example of an X-ray device.

Finally, FIG. 5 is a schematic sketch of an X-ray device 22 that may be used during medical interventions to monitor the intervention, and may include a C-arm 23 on which an X-ray source 24 and an X-ray detector 25 are arranged on opposite sides. The patient may be placed on an examination table 26 such that, as described, X-ray images of the region of interest may be recorded. In addition, the X-ray device 22 includes a control device 27, which is here only shown schematically, which is embodied to carry out the method.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a navigation image configured to display features of a region of interest of a patient, the method comprising:
    recording a first X-ray image and a mask image with an X-ray device;
    determining, by the X-ray device, a first subtraction image by subtracting the mask image from the recorded first X-ray image;
    recording a second X-ray image with the X-ray device;
    determining, by the X-ray device, a second subtraction image by subtracting the mask image or a further mask image from the recorded second X-ray image;
    determining, by the X-ray device, the navigation image by superimposing the first subtraction image and the second subtraction image; and
    outputting the navigation image on a display device,
    wherein at least one of the subtraction images is preprocessed before the superimposition by transfer from a gray-value space into a color space that is different from a color space of the other subtraction image,
    wherein the navigation image is determined in color, and
    wherein dynamics of at least one of the subtraction images are compressed.

2. The method of claim 1, further comprising:
    using the navigation image during a medical intervention.

3. The method of claim 1, wherein the first subtraction image is an image of a blood vessel system of the patient, and
    wherein the first X-ray image is recorded as a filled image with an administration of contrast medium in the blood vessel system.

4. The method of claim 3, wherein the second subtraction image is an image showing at least one medical instrument located in the blood vessel system of the patient.

5. The method of claim 4, wherein the second X-ray image is recorded cyclically.

6. The method of claim 1, wherein the second subtraction image is an image showing at least one medical instrument located in a blood vessel system of the patient.

7. The method of claim 1, wherein the first and second subtraction images are at least two disjoined color spaces or two disjoined dynamic result ranges.

8. A method for determining a navigation image configured to display features of a region of interest of a patient, the method comprising:
   recording a first X-ray image and a mask image with an X-ray device;
   determining, by the X-ray device, a first subtraction image by subtracting the mask image from the recorded first X-ray image;
   recording a second X-ray image with the X-ray device;
   determining, by the X-ray device, a second subtraction image by subtracting the mask image or a further mask image from the recorded second X-ray image;
   determining, by the X-ray device, the navigation image in color by superimposing the first subtraction image and the second subtraction image; and
   outputting the navigation image on a display device,
   wherein at least one of the subtraction images is preprocessed before the superimposition by transfer from a gray-value space into a color space that is different from a color space of the other subtraction image,
   wherein a color space extending from black to magenta is used for the second subtraction image when features contained in the second subtraction image are displayed against a dark background of the first subtraction image, or
   wherein a color space extending from white to red is used for the second subtraction image when features contained in the second subtraction image are displayed against a light background of the first subtraction image.

9. The method of claim 1, wherein, when features depicted using a first dynamic portion on a background using a second dynamic portion of an overall dynamic region, in at least one of the subtraction images on at least one of the at least one subtraction image, dynamic compression is used to suppress structures in a saturation portion of the first dynamic portion bounding the overall dynamic region and in at least one suppression portion of the second dynamic portion bounding the overall dynamic region and to intensify structures in a boundary region of the first dynamic portion positioned adjacent to the second dynamic portion.

10. The method of claim 9, wherein, when features are contained in both the first and second subtraction images in a same dynamic portion, at least one subtraction image is inverted before the superimposition within a context of the dynamic compression.

11. An apparatus comprising:
    an X-ray device configured to:
      record a first X-ray image;
      record a second X-ray image;
      record a mask image, and optionally, a further mask image;
      determine a first subtraction image by subtracting the mask image from the recorded first X-ray image;
      determine a second subtraction image by subtracting the mask image or the further mask image from the recorded second X-ray image; and
      determine the navigation image by superimposing the first subtraction image and the second subtraction image; and
    a display device configured to output the navigation image,
    wherein at least one of the subtraction images is preprocessed before the superimposition by transfer from a gray-value space into a color space that is different from a color space of the other subtraction image, and
    wherein dynamics of at least one of the subtraction images are compressed.

12. The apparatus of claim 11, wherein the X-ray device unit comprises a C-arm on an X-ray source and an X-ray detector are arranged opposite to one another.

13. A non-transitory computer-readable medium storing a program, when executed by a computing device, is configured to cause the computing device to at least perform:
    determine a first subtraction image by subtracting a mask image from a recorded first X-ray image;
    determine a second subtraction image by subtracting the mask image or a further mask image from a recorded second X-ray image;
    determine the navigation image by superimposing the first subtraction image and the second subtraction image; and
    display the navigation image,
    wherein at least one of the subtraction images is preprocessed before the superimposition by transfer from a gray-value space into a color space that is different from a color space of the other subtraction image, and
    wherein dynamics of at least one of the subtraction images are compressed.

* * * * *